(12) United States Patent
Davidson

(10) Patent No.: US 6,200,685 B1
(45) Date of Patent: *Mar. 13, 2001

(54) TITANIUM MOLYBDENUM HAFNIUM ALLOY

(76) Inventor: James A. Davidson, 1830 Cour De iberville, Germantown, TN (US) 38138

(*) Notice: Subject to any disclaimer, the term of this patent is extended or adjusted under 35 U.S.C. 154(b) by 0 days.

This patent is subject to a terminal disclaimer.

(21) Appl. No.: 09/241,812

(22) Filed: Feb. 2, 1999

Related U.S. Application Data

(63) Continuation-in-part of application No. 08/829,327, filed on Mar. 27, 1997, now Pat. No. 5,954,724.

(51) Int. Cl.$^7$ .................................................. B32B 9/00
(52) U.S. Cl. ...................... 428/472.1; 148/317; 148/421; 420/421
(58) Field of Search .................... 428/472.1; 148/317, 148/421; 420/421

(56) References Cited

U.S. PATENT DOCUMENTS

| | | |
|---|---|---|
| 2,892,706 | 6/1959 | Jaffee et al. . |
| 2,948,607 | 8/1960 | Wagener . |
| 2,987,352 | 6/1961 | Watson . |
| 3,370,946 | 2/1968 | Bertea et al. . |
| 3,408,604 | 10/1968 | Doi et al. . |
| 3,643,658 | 2/1972 | Steinemenan . |
| 3,677,795 | 7/1972 | Bokros et al. . |
| 3,752,664 | 8/1973 | Steinemann . |
| 3,777,346 | 12/1973 | Steinemann . |
| 3,849,124 | 11/1974 | Villani . |
| 3,911,783 | 10/1975 | Gapp et al. . |
| 3,969,130 | 7/1976 | Bokrus . |
| 3,994,692 | 11/1976 | Rudy ..................................... 428/336 |
| 4,040,129 | 8/1977 | Steinemann et al. . |
| 4,145,764 | 3/1979 | Suzuki et al. . |
| 4,146,936 | 4/1979 | Aoyagi et al. . |
| 4,170,990 | 10/1979 | Baumgart et al. . |
| 4,197,643 | 4/1980 | Burstone et al. . |
| 4,278,630 | 7/1981 | Scheicher . |
| 4,511,411 | 4/1985 | Brunner et al. . |
| 4,668,290 | 5/1987 | Wang et al. . |
| 4,714,468 | 12/1987 | Wang et al. . |
| 4,769,041 | 9/1988 | Morscher . |
| 4,814,011 | 3/1989 | Kamohara et al. . |
| 4,857,269 | 8/1989 | Wang et al. . |
| 4,902,359 | 2/1990 | Takeuchi et al. . |

(List continued on next page.)

FOREIGN PATENT DOCUMENTS

| | | | |
|---|---|---|---|
| 2703529 | 8/1978 | (DE) . | |
| 0437079 | 7/1991 | (EP) . | |
| 1104942 | 3/1968 | (GB) | ..................................... 420/421 |
| 1297152 | 11/1972 | (GB) | ..................................... 420/421 |
| 513101 | 5/1976 | (SU) | ..................................... 420/421 |

OTHER PUBLICATIONS

Albert B. Ferguson, Jr., et al.; The Ionization of Metal Implants in Living Tissues; The Journal of Bone and Joint Surgery, Jan. 1960; pp. 77–90, page consisting of Fig. 1 –Fig. 6.

(List continued on next page.)

Primary Examiner—Timothy M. Speer
(74) Attorney, Agent, or Firm—Fulbright & Jaworski L.L.P.

(57) ABSTRACT

This invention describes a corrosion-resistant, high-strength, low-modulus, titanium based alloy having about 5–11 weight percent Mo and about 6–15 weight percent Hf. This alloy is suitable for use in the fabrication of articles for medical and non-medical applications having low modulus, improved corrosion resistance and surface hardening. To increase strength, Cr, Si and Fe can be added in small amounts as well as increasing levels of interstitial oxygen, nitrogen or carbon. To maintain low elastic modulus, Mo can be partially substituted by Nb.

23 Claims, 5 Drawing Sheets

U.S. PATENT DOCUMENTS

| | | |
|---|---|---|
| 4,952,236 | 8/1990 | Wang et al. . |
| 4,983,184 | 1/1991 | Steinemann . |
| 5,169,597 | 12/1992 | Davidson et al. . |
| 5,232,361 | 8/1993 | Sachdeva et al. . |
| 5,415,704 | 5/1995 | Davidson ............................. 148/316 |
| 5,699,955 | 12/1997 | Shimizu ............................... 228/194 |
| 5,954,724 * | 9/1999 | Davidson ............................... 606/76 |

OTHER PUBLICATIONS

D.C. Mears; Electron–Probe Microanalysis of Tissue and Cells from Implant Areas; The Journal of Bone and Joint Surgery; Aug. 1966; pp. 567–576.

T.P. Hoar, et al; Corrosion–Resistant Alloys in Chloride Solutions: Materials for Surgical Implants; pp. 486–510. No date/month.

K.S. Jepson, et al; The Effect of Cooling Rate on the Beta Transformation in Titanium–Niobium and Titanium–Aluminium Alloys; pp. 677–690; Title Page to the Science, Technology and Application of Titanium. No date/month.

Ulrich Zwicker, et al.; Metallkundliche Probleme Und Supraleitung Bellergierungen Auf Basis Titan–Niob, Die Als Werkstoffe Für Die Herstellung Von Supraleitenden Magneten Dienen Könmen; Superconductivity and Metallurgical Problems with Titanium–Niobium Alloys Which May Serve As Materials For The Production Of Superconducting Magnets; 1970—pp. 836–847 No month.

W. Heller R. Löhberg; Einfluss Von Zusätzen Dritter Elemente Auf Das Kritische Magnetfeld Von Titan–Niob Legierungen; Journal of Less–Common Metals; Feb. 1971; pp. 265–276 No date/month.

Helmut Albert, et al.; Über Die Temperaturabhängigkeit Des Elastizitätsmoduls Von Niob–Titan–Legierungen; On the Temperature Dependence of Young's Modules of Niobium–Titanium Alloys; 1972, p. 126–131. (No month).

Karl Schuchardt et al.; Fortschritte Der Kieferund Gesichts–Chirurgie; pp. 49–56. (No date/month).

Charles J. Burstone and A. Jon Goldberg; Beta Titanium: a New Orthodontic Alloy; American Journal of Orthodontics; vol. 77, No. 2; Feb. 1980; pp. 121–132.

Donald Knittel; Titanium and Titanium Alloys; Kirk–Othmer Encyclopedia of Chemical Tech. vol. 23; 1983; pp. 98–113. No month.

E.W. Collings; Sourcebook of Titanium Alloy Superconductivity; 1983; Chapter 10—p. 342; Chapter 11—pp. 352; 357; 358; 366. No month.

E.W. Collings; Sourcebook of Titanium Alloy Superconductivity; Titanium–Niobium Base Quaternary Alloys, Chapter 13 pp. 405–412; pp. 418–419. (No date/month).

E.W. Collings; The Physical Metallurgy of Titanium Alloys; American Society for Metals, pp. 68–70 (No date/month).

E.W. Collings; The Physical Metallurgy of Titanium Alloys; Equilibrium Phases, pp. 39–48; Multicomponent Titanium–Base Alloys, p. 71; Nonequilibrium Phases, pp. 96–100 (No date/month).

E.W. Collings; The Pyhsical Metallurgy of Titanium Alloys, pp. 40–41; Equilibrium Phases, pp. 66–69; Mechanical Properties; Elastic Properties, pp. 120–121; Aging; Microstructural Phenomenology, pp. 190–191, 194–195, References, pp. 214–215; 218–219; 226–227 (No date/month).

Stanley A. Brown, D. Eng., and Katharine Merritt, Ph.D.; Evaluation of Corrosion Resistance of Biology; Feb. 13, 1986, pp. 1–3; Tables 1, 3, Figures 1, 2, 3.

R. Van Noort; Review—Titanium: The Implant Material of Today; Nov. 1987, pp. 3801–3811.

J.L. Murray; The Ti–ZR (Titanium–Zirconium) System; 1987, pp. 340–345 (No month).

J.L. Murray; The NB–TI (Niobium–Titanium) System; 1987, pp. 188–194 (No month).

Arthur J. Wilcock, Jr. on Orthodontic Wires; (JCO/Interviews), Aug. 1988; pp. 484–489.

The Japan Medical Review; vol. No. 12, Dec. 1991; Research and Development, pp. 12; 23.

William R. Proffit, D.D.S., Ph.D., et al.; Contemporary Orthodontics; Chapter 10, Mechanical Principles in Orthodontic Force Control; pp. 289–315 (No date/month).

Anthony D. Viazis, DDS, MS; Altas of Orthodontics; Principles and Clinical Applications; Chapter 6 Orthodontic Wires; pp. 153–162 (No date/month).

Daniel Eylon; Rodney R. Boyer, Donald A. Koss; Beta Titanium Alloys in the 1900's; Proceedings of a Symposium on Beta Titanium Alloys Sponsored by the Titanium Committee of TMS, held at the 1993 Annual TMS Meeting in Denver, CO, Feb. 22–24, 1993; Beta Titanium Alloys and Their Roles in the Titanium Industry; Paul J. Bania; pp. 3–14.

Tiadyne™ 3510; Teledyne Wah Chang—2 pages.

* cited by examiner

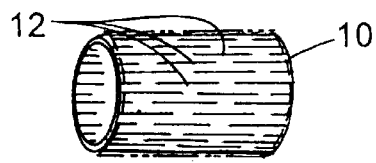
FIGURE 1A
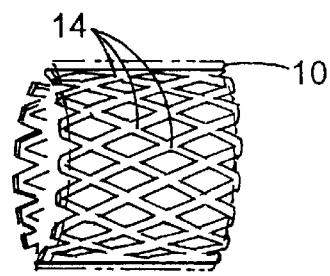
FIGURE 1B
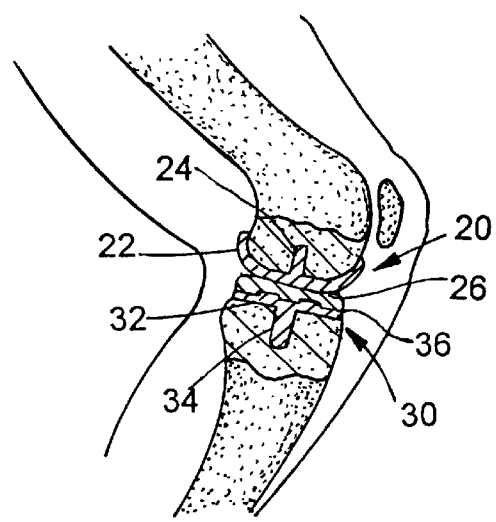
FIGURE 2A
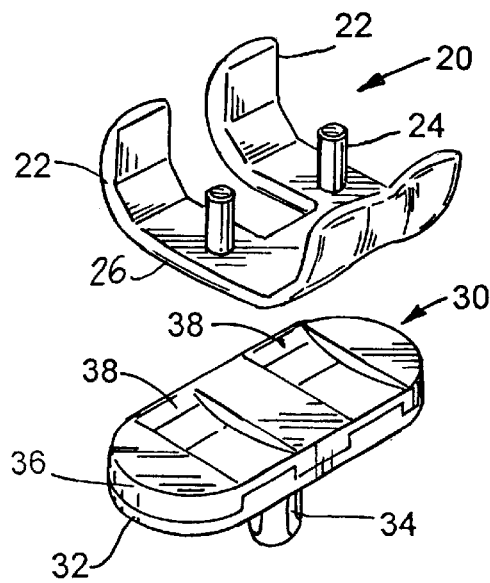
FIGURE 2B
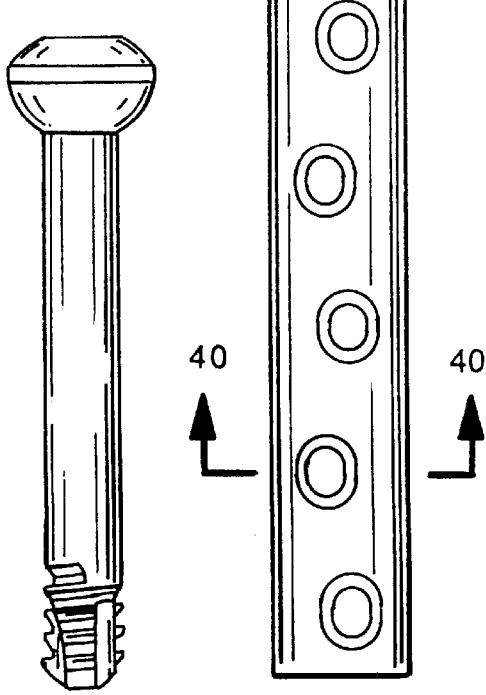
FIGURE 3A
FIGURE 3B
FIGURE 3C FIGURE 4A FIGURE 4B
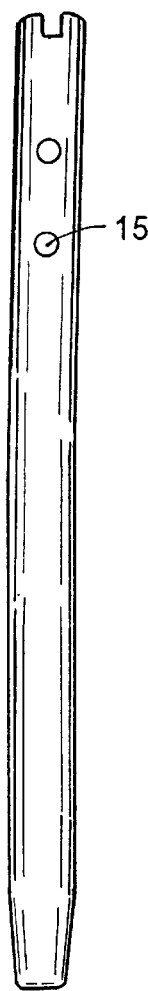
FIGURE 5
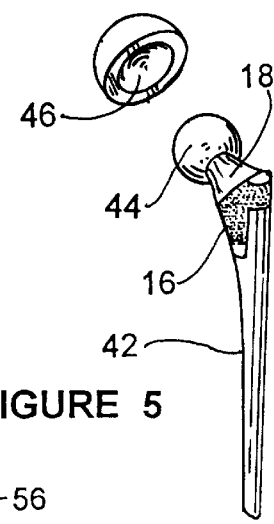
FIGURE 6
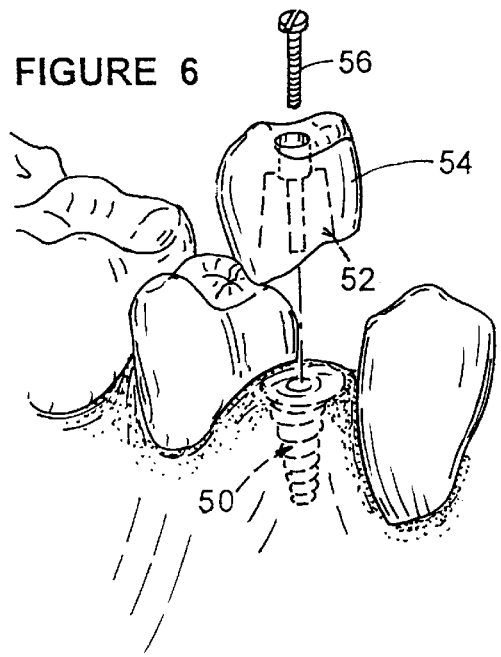
FIGURE 7B
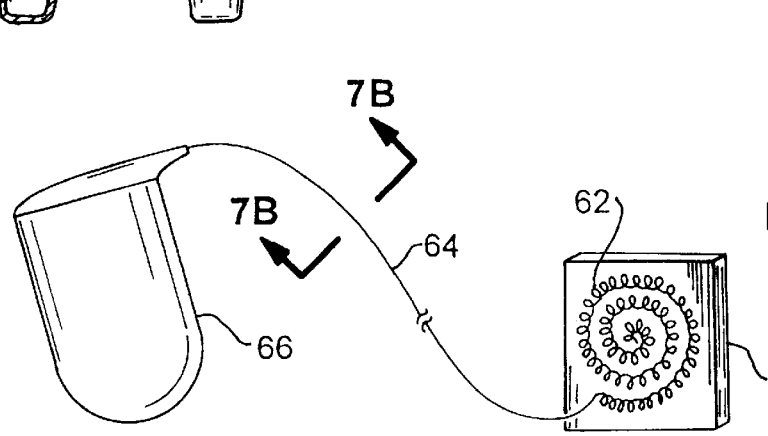
FIGURE 7A

TITANIUM MOLYBDENUM HAFNIUM ALLOY

This application is a continuation-in-part of 08/829,327, filed Mar. 27, 1997 now U.S. Pat. No. 5,954,724, issued Sep. 21, 1999.

FIELD OF THE INVENTION

The present invention relates generally to a titanium alloy and, more particularly, to a titanium alloy suitable for use in the manufacture or fabrication of a variety of structures, products or devices, or components thereof

BACKGROUND OF THE INVENTION

Alloy titanium has been used for all types of structures, including aircraft, corrosion-resistant containers and medical implants. Titanium alloys are particularly useful for components used in corrosive environments due to their excellent corrosion resistance properties compared to alternative stainless steel, nickel-base alloys, aluminum and cobalt-chrome alloys. Titanium and its alloys are more prone to fretting and wear compared to harder (Rc42–44) Co—Cr—Mo alloys and age-hardened stainless steels. However, the lower elastic modulus, in combination with high strength allows titanium alloys to be useful for applications requiring shock absorption or high levels of strain. Thus, articles or devices formed from titanium alloys possess a useful combination of strength and flexibility, and tend to exhibit good wear resistance. Additionally, current titanium alloys, although more flexible (lower modulus) than steel, nickel, or cobalt, are not equivalent in flexibility to aluminum (modulus of 10 Msi) or magnesium (modulus of 7 Msi). It would be useful to have a corrosion-resistant titanium alloy that could possess a unique combination of high-strength, lower modulus (less than 10 Msi) and with the ability to develop a high, wear-resistant bulk hardness. Greater hardness can allow for less friction and improved abrasion resistance, in contrast to the poor wear resistance of softer stainless steels or flexible titanium, aluminum and magnesium alloys.

Examples of titanium alloys with a low-modulus (less than 130 GPa) include a room temperature beta titanium alloy for wire as described in U.S. Pat. No. 4,197,643. This patent describes the use of Mo, Nb, Ta and V to produce the beta alloy, and additionally, the use of Mn, Fe, Cr, Co, Ni, Cu, Al and Zr. There is no mention of the use of hafnium in the alloys. Alloy strength is achieved by aging to precipitate the alpha phase or by cold working. The preferred composition is Ti-11.5Mo-6Zi-4.5Sn, commonly called Beta III. However, the hardness is in the 30's on the Rockwell "C" scale. U.S. Pat. No. 5,312,247 describes a shape-memory or super elastic alloy having a predetermined activation temperature. This patent further describes the use of nickel-titanium based and titanium-molybdenum based alloys but as in the previous example, does not mention the use of hafnium (Hf) in the alloys. The use of nickel-containing metals is undesirable, as its presence reduces the corrosion resistance. Nitinol is another shape-memory alloy. However, this highly elastic alloy also has less than optimum corrosion resistance with respect to other alternative available titanium alloys because of the high concentrations of nickel. Nitinol also has a relatively low hardness in the Rc 30's. U.S. Pat. No. 5,232,361 describes another series of titanium alloys formulated of at least one of a group of alloys based on Ti, Zr, Si, B, Be, Cr, Nb and Co in a composition in which at least one of these elements exists in a range of between 40 weight percent and greater than 99 weight percent. A bracket containing at least 45 weight percent titanium is given as an example. Other examples include alloys with at least 80 weight percent Ti with the addition of Al, V, Fe and/or Nb, and even a 99 weight percent Ti alloy. Once again, the use of hafnium is not described, and strength, elastic modulus, hardness, and corrosion resistance are less than optimal.

Other examples of shape memory alloys include those described in U.S. Pat. Nos. 4,665,906 and 5,067,957 which describe devices and methods of installation using a non-specific shape memory alloy which displays stress induced martensitic behavior, versus an activation temperature. The present inventive Ti alloy does not exhibit shape memory behavior, and contains hafnium to improve corrosion resistance. Additionally, unlike prior art Ti alloys described above, the presence of hafnium allows the option of surface hardening of the alloy via a conversion surface oxide, nitride, carbide, or combination of these.

An early example of an improved titanium alloy for implants was discussed in U.S. Pat. No. 4,040,129 in which bone and dental implants having full tissue compatibility were described as being composed of a first component of about 3 to 30 weight percent selected from the group Nb, Ta, Cr, Mo and/or Al, and a second component of Ti and/or Zr; wherein the sum of the Cr, Mo and Al is less than 20 weight percent and the weights of Ti and/or Zr is less than 75 weight percent. This alloy was also free of Cu, Co, Ni, V and Sn. Examples described in the patent include Ti-9Nb-11Cr-3Al and Ti-4Mo-48Zr.

Additionally, in U.S. Pat. No. 4,040,129, the benefit and desirability of a lower elastic modulus of the described alloy was not discussed, nor was there any mention of the use of hafnium in the composition. A more recent patent, U.S. Pat. No. 4,857,269, also deals with the desirability of low elastic modulus in medical devices. This patent describes a titanium based alloy consisting of an amount of up to 24 weight percent of isomorphous beta stabilizers Mo, Ta, Nb and Zr, providing that molybdenum, when present, is at least 10 weight percent, and when present with zirconium, is between 10 and 13 weight percent with the zirconium being between 5 and 7 weight percent. Additionally, the same titanium based alloy also has up to 3 weight percent eutectoid beta stabilizers selected from Fe, Mn, Cr, Co and Ni, wherein the combined amount of isomorphous and eutectoid beta stabilizers is at least 1.2 weight percent. Optionally, up to 3 weight percent aluminum and lanthanum can be present in the alloy with the elastic modulus not exceeding 14.5 Msi. Examples include Ti-10-20Nb-1-4Zr-2Fe-0.5Al (TMZF)™. Once again, less than optimum elements (Mn, Co, Ni, Al), from a corrosion standpoint, are found in the alloy composition and there is no mention of hafnium or the ability to be surface hardened.

Hoars and Mears (1966) and Pourbaix (1984), based on electrochemical stability, suggested the use of Ti, Nb, Zr, and Ta as elemental constituents for improved corrosion resistance. However, it is important to note that Ti—Mo alloys were also included as acceptable materials and this was supported by comparative corrosion data between Ti and Ti-16Mo-3Nb-3Al in which the Ti—Mo alloy showed improved corrosion resistance. Thus, the presence of Mo in titanium alloys can actually be beneficial from the standpoint of corrosion. It has also been reported in the titanium literature (Titanium Alloys, E. W. Collings, ASM, 1986) that the addition of more than about 4 weight percent molybdenum improved the corrosion resistance of titanium, particularly in crevice-type environments. With many of device service applications requiring assembled components in corrosive environments, the presence of molybdenum can be beneficial in a titanium alloy.

In an effort to improve the corrosion resistance properties of the titanium alloy and to reduce its elastic modulus, Davidson and Kovacs (U.S. Pat. No. 5,169,597) developed a medical implant titanium alloy with 10–20 weight percent Nb, or 30–50 weight percent Nb and 13–20 weight percent Zr, or sufficient Nb and/or Zr to act as a beta stabilizer by slowing transformation of beta (U.S. Pat. No. 5,545,227). The preferred example is Ti-13Nb-13Zr (Ti1313™). Tantalum can also be used as a replacement for niobium where the sum of Nb and Ta is 10–20 weight percent of the alloy. Subsequent continuation-in-part patents and applications, describing this type of alloy for other medical device applications also exist and are considered herein with respect to prior art. All of these patents and applications describe the use of Ti, Nb, and/or Zr. However, the use of hafnium, molybdenum, the combination of Hf and Mo, or small quantities of selected strengthening elements is either not described or is specifically excluded. Further, the issue of hardness is not addressed, and the preferred composition (Ti-13Nb-13Zr) has a bulk hardness of only 33 Rc and even lower (Rc 24) in the quenched condition. Others, such as I. A. Okazaki, T. Tateishi and Y. Ito, have also proposed similar compositions including Ti-15Zr-4Nb-2Ta-0.2Pd and variations of the type Ti-5Zr-8Nb-2Ta-10-15-Zr-4-8-Nb-2-4Ta, Ti-10-20Sn-4-8Nb-2Ta-0.2Pd, and Ti-10-20Zr-4-8Nb-0.2Pd. None however, addresses hardness, the inclusion of hafnium or the ability to be surface hardened.

Teledyne Wah Chang Albany, a major supplier of titanium, zirconium, niobium and their alloys, developed a Ti-35Nb-10Zr alloy. Due to the excellent biocompatibility of hafnium (1994 Teledyne Annual Report), Teledyne also developed titanium based alloys which include niobium and hafnium and a stiff, hard, Hf-based alloy as a replacement for Co—Cr—Mo bearing alloys. However, in the Teledyne annual report, no mention was given of molybdenum and its ability to reduce elastic modulus or the use of hafnium to improve corrosion resistance, nor its ability to be surface hardened. Neither was there any mention of incorporating hatnium with molybdenum in titanium alloys. This is due, most likely, to the general perception that molybdenum relates to less than optimum corrosion resistance. However, as mentioned previously, other studies have shown that molybdenum, combined with titanium, can have excellent corrosion resistance. Similarly important is the fact that molybdenum can reduce the elastic modulus of the alloy.

TItanium alloys have lower hardness than, for example, Co—Cr alloys and stainless steels. Due to this property, many investigators have studied and reported methods to harden titanium alloys, primarily through surface hardening processes. In addition to the improved bulk hardness of the inventive alloy, the inventive alloy is also designed to be surface hardened. The improved bulk hardness further improves the attachment strength of the surface coating formed, in part, from the presence of the hafnium in the composition of the inventive alloy. Prior art surface hardening methods include a wide range of overlay coating methods such as chemical and physical vapor deposition methods. These methods, however, require too high or too low a temperature that results in metallurgical changes and less than optimum attachment of the hard, deposited, surface coating or require the use of an interlayer to improve attachment of the hard surface coating. Oxidation and nitriding methods can form a natural conversion surface oxide or nitride with a hard, built-in oxygen or oxygen rich, hardened metal interlayer. Examples of these are described in U.S. Pat. No. 5,372,660 for zirconium-containing titanium alloys, U.S. Pat. No. 5,037,438 for oxygen surface hardening of Zr and Zr—Nb alloys for bearing surfaces, and U.S. Pat. No. 5,152,794 for oxidation and nitriding of zirconium or zirconium alloy devices with a surface layer 1–5 microns thick. Other similar patents exist for zirconium-containing titanium alloys and Zr—Nb alloys used in medical implant devices. See, for example, U.S. Pat. Nos. 5,282,852; 5,370,694 and 5,496,359. Internal oxidation is also described in U.S. Pat. No. 5,415,704, whereas U.S. Pat. No. 5,498,302 describes internal nitridization methods to harden a surface, but without the presence of a hard outer oxide or nitride layer. Unlike oxygen or nitrogen diffusion methods which produce interstitial strengthening of the metal, internal oxidization or nitridization, using solute levels of more oxidizable or nitridable elements in quantities less than 2 weight percent, actually forms submicron oxide or nitride dispersions to produce the hardening.

Other nitridizing processes to harden the surface of a metal are described in U.S. Pat. No. 5,419,984 for stainless steel, in U.S. Pat. No. 4,511,411 for titanium alloys using an autoclave containing nitrogen, and U.S. Pat. No. 5,334,264 which uses enhanced plasma nitriding methods. There are also studies of oxygen diffusion hardening of Ti, Ti-6Al-4V and Ti-6Nb-7V alloys (Streicher), and the use of N-ion implantation (Sioshanchi) which produces a much less effectively hardened and non-uniform surface. A wide variety of surface nitriding and oxidization options are available and known to those skilled in the art.

Studies by Wallwork and Jenkins, 1959, exist on the oxidation of zirconium alloys, titanium alloys and hafnium showing the oxidation of hafnium producing a hard, well attached conversion surface oxide diffusion bonded to the metal substrate. However, these oxidation characteristics were obtained in an effort to reduce (resist) this process, and not to intentionally form the surface oxide to form a hard, protective, wear-resistant surface layer. Bania and Parris (Timet, Inc., Beta 215, Vol. II, 1990 Ti Conf.) investigated various Ti—Mo, Ti—Cr, Ti—Hf, Ti—Nb alloys and other alloys with respect to oxidation resistance that leads to the optimum composition of the beta 215 alloy (Ti-15Mo-2.8Nb-3Al). Specific combinations of Ti, Mo, and Hf were not investigated for applications with optimal combinations of strength, hardness, and elastic modulus. Although not related to reducing elastic modulus or aqueous corrosion resistance, Bania and Parris have shown that the addition of 15 weight percent molybdenum reduced the oxidation resistance of Ti-15Mo-5Zr versus pure Ti. Further, the addition of 5 weight percent Hf reduced oxidation resistance to a greater degree in Ti-15Mo-5Hf. An alloy of Ti-15Cr-5Mo and Ti-15Cr also showed substantially improved oxidation resistance versus a Ti or Ti-15Mo-5Zr alloy. The best oxidation resistance in this study was exhibited by Ti-15Mo-2-5Nb, and the addition of 3 weight percent Al further improved oxidation resistance, hence the development of Ti-21S. The use of this alloy, Ti-21S, has also been proposed for medical implants (Bitambri and Shetty, 1994 Soc. Biomat. Pg. 195). However, Ti-21S exhibits only a marginal reduction in elastic modulus in the age-hardened condition compared to most titanium alloys.

SUMMARY OF THE INVENTION

The above discussion illustrates the non-obviousness of Ti—Mo—Hf compositions, according to the present invention, as being useful for various device applications.

The present invention is a titanium based alloy suitable for use in the fabrication of a variety of articles, or components thereof , (i.e., structures, products, and devices) including (but not limited to) the following: cables, fasteners, gears, valves, chains, springs, sporting equipment, marine and fishing devices, oilfield equipment, cutting devices, pressure vessels, and automotive, aircraft/aeronautic and train components. The inventive alloy is also suitable for structures, products, and devices in oil/sour gas applications, chemical processing, metal plating, and other applications. The inventive alloy is also suitable for use in the fabrication of articles for medical applications such as medical implants, instruments, and related devices. The inventive alloy is a highly corrosion-resistant high-strength, low-modulus, high-hardness titanium based alloy having about 5–11 weight percent Mo and about 6–15 weight percent Hf. Optionally, to further increase strength, Cr, Si and Fe can be added at levels less than about 3 weight percent. In addition, interstitial oxygen, nitrogen or carbon can be added for interstitial strengthening. To reduce or maintain the relatively lower elastic modulus of the alloy, Mo can be partially substituted by Nb. Thus, articles or components manufactured from the inventive alloy exhibit improved corrosion resistance, fretting resistance, and an ability to be surface hardened. Further, through localized or selective heat treatment, an article or component thereof may be fabricated to have local regions of high strength and low modulus, and other regions exhibit high-strength and high hardness properties. The inventive alloy, with its unique combination of corrosion resistance, strength, modulus, and bulk hardness may be suitable for use in additional applications not described herein but are contemplated by the present invention.

BRIEF DESCRIPTION OF THE DRAWINGS

The invention will become more apparent when the detailed description of exemplary embodiments is considered in conjunction with the appended drawings, in which:

FIG. 1A is a schematic diagram of a self-expanding stent according to the invention, positioned within a segment of a blood vessel to be opened, in a first, non-deformed configuration; and FIG. 1B is a perspective view illustrating the stent of FIG. 1A after expansion when released from the delivery catheter;

FIG. 2A is a schematic diagram of a knee joint prosthesis in place;

FIG. 2B is a schematic diagram of the parts of a typical knee joint.

FIG. 3A is a schematic diagram of a typical screw for affixing bone plates;

FIG. 3B is a diagram of a typical bone plate;

FIG. 3C is a cross-section of FIG. 3B taken along line 40;

FIG. 4A is a schematic diagram of a side view of a typical intramedullary rod used in orthopedic applications;

FIG. 4B is a view of FIG. 4A rotated by 90°;

FIG. 5 is a schematic diagram showing components of a typical hip joint prosthesis;

FIG. 6 shows a partial cross section of a gum with a dental implant fabricated from the titanium alloy according to the present invention, wherein the root of the implant is implanted into the jawbone, an abutment of the inventive alloy projects above the gumline for receiving the crown, a porcelain veneer in tooth-shape attaches to an implant with an abutment screw, fabricated from the inventive alloy;

FIG. 7A is a schematic diagram of the components of a defibrillator, showing power source, lead wire, and polymeric patch with coiled electrode;

FIG. 7B is a cross-section of the lead wire of FIG. 7A;

DETAILED DESCRIPTION OF PREFERRED EMBODIMENTS

Figure 8:
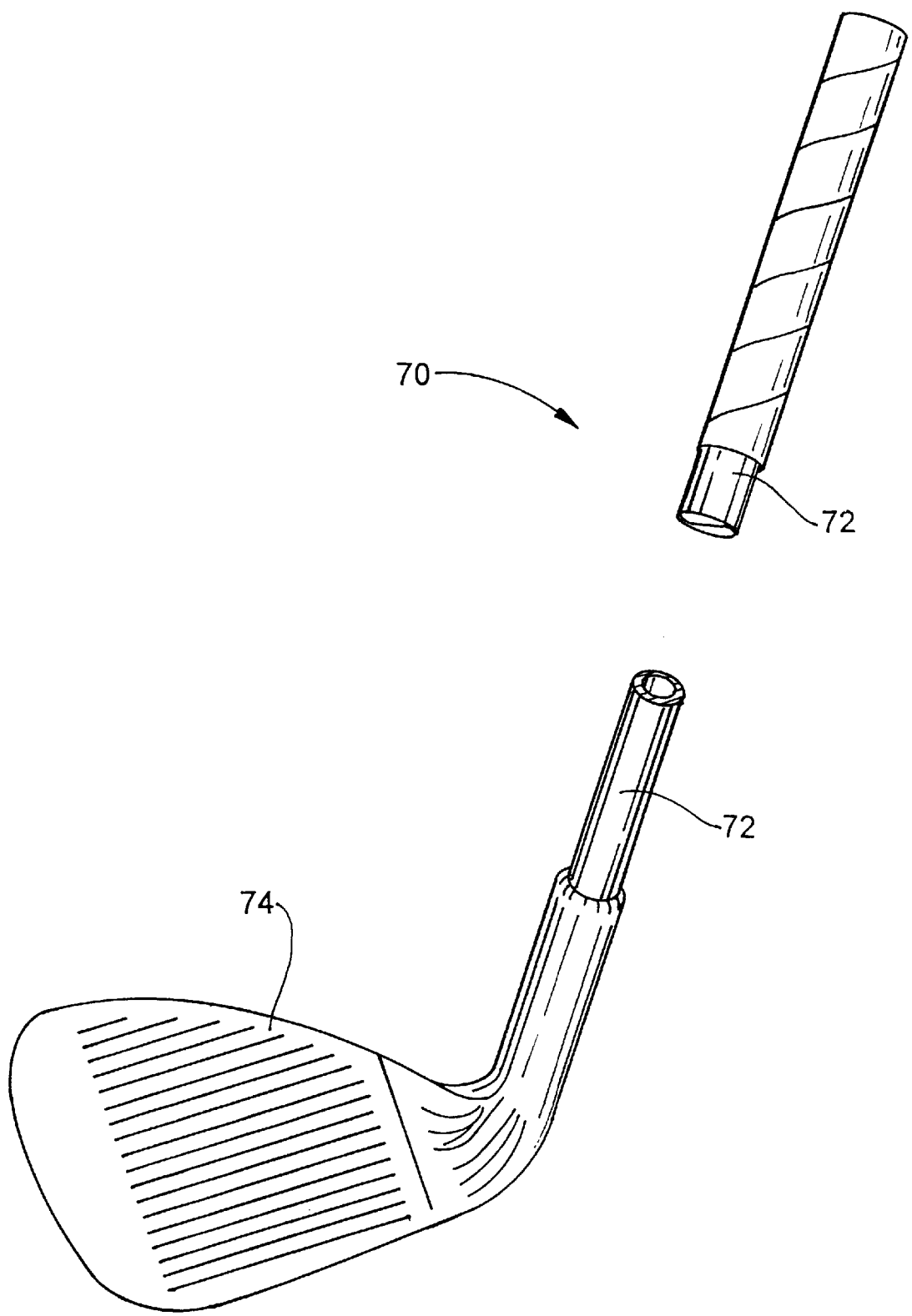
FIG. 8 is a perspective view of a golf club iron according to the invention.

The inventive alloy can be produced by combining as commercially pure components, titanium, molybdenum and hafnium in the appropriate proportions. The method for titanium alloy production, such as casting, powder metallurgy, etc. are well known to those of ordinary skill in the art of metallurgy and the production of the alloy requires no special skills or precautions beyond the materials, proportions and techniques described below.

The present invention comprises a biocompatible, radiopaque, high-strength, low-modulus, high-hardness titanium base alloy for the manufacture of articles having improved corrosion resistance due to the combined addition of 5–11 weight percent molybdenum (Mo) and about 6–15 weight percent hafnium (Hf) which additionally allows for the surface hardening of a medical implant or device manufactured from the inventive alloy. If desired, the amount of molybdenum can be adjusted such that the elastic modulus of the alloy is minimized. In one preferred embodiment, the titanium alloy composition is titanium, 7 weight percent Mo and 7 weight percent Hf which has an as-quenched modulus of 12 Msi (vs 16.5 for Ti-6Al-4V) and an aged strength of 190 Ksi (vs. 173 Ksi for TMZF™ and only 145 Ksi for Ti1313™). Substitution of molybdenum with niobium is also incorporated within the scope of the invention, wherein niobium partially substitutes for the molybdenum in the alloy.

The inventive alloy can be quenched from the above reduced beta transus (reduced to less than about 830° C. by the presence of Mo and Hf) to form a martensite that can be easily cold or warm worked and can respond to age hardening. Such cold- or warm-working of the inventive alloy can also increase strength and reduce the elastic modulus, and is known by those skilled in the art. The amount of hafnium added to the alloy is of an amount sufficient to assist with the stabilization of the beta phase via lowering of the beta transus to improve strength and bulk hardness, improve corrosion resistance, provide improved radiopacity, and to form a hard, abrasion-resistant conversion surface oxide or nitride through standard oxidation and nitridization methods, known by those skilled in the art. The presence of a hard, inert, abrasion resistant ceramic surface layer in the inventive alloy, particularly in combination with improved bulk hardness, presents an important option for articles in which it is desirable to have lower friction and wear, improved cutting ability, electrical insulation, and improved corrosion resistance. This improved oxidation resistance of the inventive alloy is a reflection of the ability of hafnium to more readily oxidize and control the surface layer properties than zirconium and thus, lower the potential for hydrogen to diffuse into the alloy, if hydrogen is present during a conversion hardening process. Hydrogen can be detrimental to titanium alloys by the potential formation of hydrides formed during the conversion hardening process. Typical conversion hardening temperatures for the inventive alloy include a range from between about 300 to 700° C. for oxidation and from a range between about 700 to 1100° C. for nitridization. The time at temperature can be varied depending on the desired amount of oxide or nitride on the surface.

Various properties of hafnium, titanium and molybdenum are given in Table I in comparison to other group 4, 5, 6 and 8 transition metals.

TABLE I

Selected Transition Elements and Their Properties

| ELEMENT (Group No.) | Ti (4) | Zr (4) | Hf (4) | V (5) | Nb (5) | Ta (5) | Cr (6) | Mo (6) | Fe (8) |
|---|---|---|---|---|---|---|---|---|---|
| Atomic No. | 22 | 40 | 72 | 23 | 41 | 73 | 24 | 42 | 26 |
| Crystal Structure | HCP | HCP | HCP | BCC | BCC | BCC | BCC | BCC | BCC |
| Atomic Radius (D) | 1.458 | 1.58 | 1.59 | 1.32 | 1.43 | 1.43 | 1.25 | 1.36 | 1.24 |
| Melt Temp (° C.) | 1670 | 1855 | 2231 | 1910 | 2469 | 3020 | 1890 | 2625 | 1539 |
| Atomic Weight | 47.90 | 91.22 | 178.5 | 50.94 | 92.91 | 180.95 | 52.00 | 95.94 | 55.85 |
| Density (g/cm$^3$) | 4.54 | 6.5 | 11.4 | 6.0 | 8.57 | 16.6 | 7.19 | 10.2 | 7.87 |
| Elastic Modulus (GPa) | 107 | 100 | 137 | 138 | 103 | 186 | 289 | 324 | 200 |
| Tensile Str. (MPa) | 240 | 289 | 445 | 496 | NA | 414 | NA | 655 | NA |
| ΔG (oxide) K Cal. | 280 | 300 | 334 | 137 | 120 | 644 | 323 | 180 | 63 |
| ΔG (nitride) K Cal. | 160 | 195 | 165 | 130 | 114 | 119 | 52 | 34 | 2 |
| Valence (common) | 4 | 4 | 4 | 3,5 | 5 | 5 | 3 | 4,6 | 2,3 |
| Ratio: Vol. Ox/Vol. metal | 1.76 | 1.57 | 1.62 | 1.85 | 2.74 | 2.47 | 2.02 | 3.27 | 2.20 |
| Mag. Susceptibility 10$^{-6}$ ergs | 153 | 122 | 75 | 255 | 195 | 154 | 180 | 89 | >15,000 (mag.) |

Table I shows that the valence, atomic radius and crystal structure of hafnium is very comparable of that of zirconium. As mentioned previously, it is often referred to as the sister element of zirconium. However, the free energy of formation of the oxide is greater for hafnium than for zirconium, which should result in improved surface hardening and corrosion resistance. Hafnium, being further away from titanium in the periodic table than zirconium, should improve substitutional solid solution strengthening and bulk hardening. The magnetic susceptibility of hafnium is also lower than zirconium, which may improve the magnetic and electrical characteristics of the article manufactured from the inventive alloy. Further, under oxidation and nitriding, hafnium will produce oxide or nitride attachment strength and abrasion resistance comparable to zirconium due to the similar ratios of oxide to metal volumes. However, with improved bulk hardness of the inventive alloy, the surface oxide or nitride can be expected to have improved abrasion resistance due to a lower stress concentration between the surface layer and metal substrate. In addition, the alloy can be hot or cold mechanically worked to optimize grain size, strength, elastic modulus, and eh toughness. Cold working in the softer, lower-modulus as-quenched condition can further reduce modulus as well as increase strength (especially if aged in the cold-worked condition).

The addition of niobium to a titanium alloy can reduce the elastic modulus of the alloy with a minimum at about 16 weight percent Nb. However, the presence of molybdenum in a titanium alloy can also reduce the elastic modulus with a minimum at about 6 weight percent Mo as well as improve corrosion resistance of an implant manufactured from the inventive alloy, particularly in reducing-type, low pH environments, such as those created by passive oxide film damage in crevices and sour-gas environments. Zirconium can improve corrosion resistance, however, hafnium improves corrosion resistance in the alloy to a greater degree in oxidizing high pH environments. This phenomenon is well described by Pourbaix. Although niobium and zirconium in a titanium alloy can be beneficial with respect to medical devices, the novel combination of molybdenum and hafnium can be expected to provide even greater benefits in a titanium alloy.

Metallurgically, zirconium can provide marginal strengthening of titanium alloys, but hafnium can provide slightly more strengthening and improved bulk hardening. Both stabilize the alpha and beta phase, and thus lower the beta transus via a more sluggish transformation. However, niobium is a weaker beta stabilizer than molybdenum. Formability of an alloy improves if the beta transus can be lowered such that a martensitic transformation occurs following rapid cooling or quenching. In this regard molybdenum is more effective than niobium. This martensitic structure can also allow the alloy to be aged hardened which can occur simultaneously with formation of a hard conversion oxide or nitride surface. An amount of about a 13 weight percent of niobium is required to produce a martensitic start (Ms) temperature of 600 degrees C., while only 6 weight percent of molybdenum is required. Further, molybdenum provides almost twice the strengthening and hardening of titanium as compared to niobium. In a titanium alloy including molybdenum above about 11 weight percent, transformation-aided ductility can also result. Orthorhombic (alpha double prime) martensite can result during quenching of a titanium alloy that includes molybdenum above about a 4 weight percent. However, more than 10 weight percent niobium is required, or 26 weight percent tantalum, to accomplish the same response in a titanium alloy. In a titanium alloy, molybdenum greater than about 6 weight percent is required in order to minimize or eliminate any untransformed beta. The beta transus for this level of molybdenum (6 weight percent) is less than about 850° C., and upon quenching, a fine dispersion of hexagonal omega phase precipitates can result. The addition of zirconium or hafnium can retard this omega process. The small size (25 angstroms) of the omega phase, however, can provide strengthening and hardening. Omega more readily forms in titanium alloys for molybdenum levels above about 8 weight percent. Because omega phase precipitation and hardening can also occur as a result of air-cooling above the beta transus, the composition of the inventive alloy has been selected to also allow for this method of bulk hardening and strengthening. This is particularly useful if high-strength, low modulus cold-worked articles are to be selectively heated and air-cooled to produce localized areas of high strength and high bulk hardness.

The ability of the titanium alloy to age harden improves with a lower beta transus, thereby allowing for articles with thicker cross sections to transform more completely to martensite upon cooling. The stronger beta stabilizing effect of molybdenum favors improved hardenability of the inventive alloy. That is, regions near the center of larger cross-section devices have an improved ability to be effectively quenched, and thus age-hardened, with improved hardenability. The titanium alloy including molybdenum above about 28 weight percent remains essentially a beta structure. With molybdenum between 9–11 weight percent, stress induced transformation of untransformed martensite can occur, and between 11–15 weight percent Mo, stress-induced twinning can occur.

Because of the advantages and limitations described above, the preferred titanium alloy composition includes titanium with about between 5–11 weight percent molybdenum and with about 6–15 weight percent hafnium. Additionally, niobium can be substituted for molybdenum. At least one element selected from the group consisting of iron, chromium and silicon, each at levels of less than about 3 weight percent, can be optionally included in the composition for strengthening of the titanium alloy. Further, interstitial oxygen, nitrogen, or carbon can be increased for additional interstitial strengthening of the inventive alloy.

Table II provides a summary of mechanical test data and hardness data for selected Ti—Mo—Hf and Ti—Mo—Nb—Hf compositions described by the present invention. Both the as quenched (from about 830° C.) and aged (6 hours, 500° C.) are given. Table II illustrates the unique combination of low modulus (12–17 Msi), high strength (above 125 Ksi) and high hardness (above about 35 Rc) of the inventive alloy.

TABLE II

| | Tensile and Hardness Data | | | | | | |
|---|---|---|---|---|---|---|---|
| Composition (wt. %) | Condition | UTS[1] (Ksi) | Y.S.[2] (Ksi) | Percent Elong. | % Red. Area | Rc[3] | Modulus (Msi) |
| Ti—5Mo—7Hf | WQ[4] | 144 | 124 | 14.1 | 33.2 | 29 | 15.9 |
| Ti—5Mo—7Hf | Aged | 150 | 130 | 15.6 | 54.9 | 37 | 16.2 |
| Ti—7Mo—7Hf | WQ | 136 | 100 | 30 | 50 | 26 | 12.0 |
| Ti—7Mo—7Hf | Aged | 190 | 166 | 6.3 | 3.8 | 45 | 15.6 |
| Ti—9Mo—7Hf | WQ | 123 | 112 | 37.5 | 54.9 | 36 | 16.3 |
| Ti—9Mo—7Hf | Aged | 191 | 179 | 6.3 | 8.9 | 42 | 16.6 |
| Ti—9Mo—9Hf | WQ | 119 | 106 | 43.8 | 62.4 | 40 | 15.5 |
| Ti—9Mo—9Hf | Aged | 184 | 174 | 3.1 | 0.6 | 46 | 17.5 |
| Ti—7Mo—7Nb—1Fe | WQ | 150 | 150 | NA | 1.9 | 24 | 16.4 |
| Ti—7Mo—7Nb—1Fe | Aged | 197 | 184 | 6.3 | 1.9 | 44 | 17.1 |
| Ti—5Mo—4Nb—7Hf | WQ | 137 | 96 | 17.2 | 18.1 | 44 | 11.8 |
| Ti—5Mo—4Nb—7Hf | Aged | 176 | 151 | 6.3 | 10.1 | 44 | 14.8 |
| Ti—7Mo—7Nb—7Hf | WQ | 114 | 90 | 40.6 | 59.4 | 36 | 14.7 |
| Ti—7Mo—7Nb—7Hf | Aged | 177 | 165 | 4.7 | 2.4 | 43 | 16.7 |

TABLE II-continued

Tensile and Hardness Data

| Composition (wt. %) | Condition | UTS[1] (Ksi) | Y.S.[2] (Ksi) | Percent Elong. | % Red. Area | Rc[3] | Modulus (Msi) |
|---|---|---|---|---|---|---|---|
| Ti—6Mo—15Nb—6Hf | WQ | 105 | 83 | 45.8 | 57.8 | 29 | 14.5 |
| Ti—6Mo—15Nb—6Hf | Aged | 172 | 158 | 6.3 | 5.9 | 40 | 14.2 |

[1]UTS = Ultimate Tensile Strength
[2]Y.S. = Yield Strength
[3]Rc = Rockwell "C scale" hardness
[4]WQ = Water Quenched from about 900° C.

Table III shows comparison of selected compositions of the inventive alloy with other titanium alloys, Co—Cr—Mo, and 316L stainless steel (S.S.).

TABLE III

New Ti—Mo—Hf Alloys Comparisons

| Material | Condition | U.T.S.[1] (Ksi) | Percent Elongation | Modulus (Msi) | Rc[2] |
|---|---|---|---|---|---|
| 316 L S.S. | Annealed | 87 | 40 | 29 | 10 |
| 316 L S.S. | Cold Worked | 138 | 30 | 29 | 33 |
| Co Cr Mo | Cast | 115 | 8 | 31 | 44 |
| C.P. Ti | Grade 2 | 96 | 20 | 15.5 | 20's |
| Ti—6Al—4V | Annealed | 143 | 13 | 16.5 | 34 |
| Ti—6Al—4V | Forged | 160 | 8 | 16.5 | 34 |
| Ti—6Al—7Nb | Protasul 100 | 150 | 12 | 16 | 30's |
| TMZF ™ | Annealed | 155 | 20 | 13 | 30's |
| TMZF ™ | Aged | 173 | 3 | 15 | 42 |
| Ti—13Nb—13Zr | WQ[3] | 107 | 24 | 9.5 | 24 |
| Ti—13Nb—13Zr | Aged | 145 | 12 | 12 | 33 |
| Ti3510 | WQ | 82 | 18 | 10 | 30's |
| Ti3510 | Aged | 150 | 10 | 12 | 30's |
| Ti—7Mo—7Hf | WQ | 135 | 30 | 12 | 29 |
| Ti—7Mo—7Hf | WQ/Aged | 190 | 6 | 15.5 | 46 |
| Ti—7Mo—7Hf | 63% CW[4] | 195 | 3 | 8 | 32 |
| Ti—7Mo—7Hf | CW[4]/Aged | 220 | 1 | 15.5 | 47 |
| Ti—7Mo—7Hf—1Fe | WQ | 150 | — | 16.5 | 24 |
| Ti—7Mo—7Hf—1Fe | Aged | 197 | 6 | 17 | 44 |
| Ti—9Mo—7Hf | WQ | 123 | 37 | 16 | 36 |
| Ti—9Mo—7Hf | Aged | 191 | 6 | 16.5 | 42 |
| Ti—5Mo—7Hf | WQ | 144 | 14 | 16 | 29 |
| Ti—5Mo—7Hf | Aged | 150 | 16 | 16 | 37 |
| Ti—11.5Mo—6Zr—4.5Sn | Beta III, Aged | 140–180 | 13–7 | 15 | 30's |
| Ti—3Al—8V—5Cr—4Mo—4Zr | Beta C, Annealed | 125 | 13 | 15 | 30's |
| Ti—3Al—8V—5Cr—4Mo—4Zr | Aged | 180 | 7 | 15.5 | 30's |

[1]UTS = Ultimate Tensile Strength
[2]Rc = Rockwell "C scale" hardness
[3]WQ = Water Quenched from 900° C.
[4]CW = Cold Worked The inventive alloy is suitable for use in the manufacture or fabrication of a variety of structures, products or devices. These products, structures or devices include those in medical and non-medical applications.

Use of Inventive Alloy in Medical Applications

The inventive alloy is useful in the manufacture or fabrication of a variety of medical implants and devices. The manufacture of medical devices from the inventive alloy includes cardiovascular devices such as vascular and other stents, percutaneous devices, vena cava filters, annuloplasty rings, vascular and other grafts, aneurysm clips and coils, heart valves, artificial hearts and ventricular assist devices, pacemakers and electrical signal carrying leads, power containers, sensors, and percutaneous devices. The manufacture of medical devices also includes implants such as orthopaedic implants, fracture plates, compression hip plates and screws, screws, staples and various internal and external tissue fixation devices, ENT devices, joint and surface replacements, and intramedullary rods. Similarly the inventive alloy is useful for neuro devices, bone graft substitute, dental implants and devices, orthodontic devices, various surgical instruments including cutting instruments, needles, guide and delivery wires and couplers, flexible catheters, and surgical cables. To improve biocompatibility of the medical implant or device made from the inventive alloy, at least a portion of the surface of the inventive alloy can be conversion surface hardened and/or coated. Such coatings can include, but are not limited to, antibiotics, pro- or anti-thrombogenic agents, anti-inflammatory agents, morphogenic proteins, morphogenic peptides, growth factors, or stem cells.

Selected examples of implants which can be made using the inventive Ti alloy are described below and include vascular stent devices. Additional medical devices manufactured from the inventive alloy include trauma plate and intramedullary rod devices, an orthopaedic hip replacement, a dental tooth replacement implant, and a pacemaker or defibrillator lead wire.

Certain aspects of the invention may be more readily understood with reference to the accompanying figures, all of which are not to scale but for illustrative purposes only.

FIG. 1A shows an expandable stent 10 having a plurality of longitudinal slots 12 in a first, collapsed, non-expanded configuration. FIG. 1B is a perspective view illustrating the stent of FIG. 1A after expansion occurs following release within the vessel, creating a lattice-like structure of expanded material. In the case of a woven self-expanding stent construct, the expanded material forms a lattice created by the interconnection of the geometric wire centers 14.

A typical knee joint prosthesis fabricated from the inventive alloy is shown in situ in FIG. 2A or composed of the parts shown in FIG. 2B. The knee joint includes a femoral component 20 and a tibial component 30. The patella component is not shown. The femoral component includes condyles 22 which provide the articulating surface of the femoral component and pegs 24 for affixing the femoral component to the femur. The tibial component 30 includes a tibial base 32 with a peg 34 for mounting the tibial base onto the tibia. A tibial platform 36, typically a polymer bearing material, is mounted atop the tibial base 32 and is supplied with grooves 38 similar to the shape of the condyles 22. The bottom surfaces of the condyles 26 contact the tibial platform's grooves 38 so that the condyles articulate within these grooves against the tibial platform.

FIG. 3A shows a typical bone screw manufactured from the inventive alloy. FIG. 3B shows a typical plate affixed by the screws. FIG. 3C is a cross-sectional view of the bone plate shown in FIG. 3B taken along line 40.

FIG. 4A is a schematic diagram of a side view of a typical intramedullary rod used in orthopedic applications made from the inventive titanium alloy. FIG. 4B is a view of the intramedullary rod shown in FIG. 4A rotated by 90°. Holes (15) in the rod are for receiving bone screws or lag screws.

A typical hip joint assembly fabricated from the inventive alloy is shown in is FIG. 5. The hip joint stem 42 fits into the femur while the femoral head 44 of the prosthesis fits into and articulates against the inner polymer lining 46 of an acetabular cup 48 which in turn is affixed to the pelvis (not shown). A porous metal bead or wire mesh coating 16 may be incorporated to allow stabilization of the implant by in growth of surrounding tissue into the porous coating. Similarly, such a coating can also be applied to the acetabular component. The femoral head 44 may be an integral part of the hip joint stem 42 or may be a separate component mounted upon a conical taper at the end of the neck 18 of the hip joint prosthesis.

FIG. 6 shows a fixture 50 of the inventive alloy implanted into a jaw bone. The fixture 50 is capped with an abutment 52 of the inventive alloy for receiving a crown 54. In a typical implantation procedure, assuming that the original tooth has been removed, an incision is made into the gum above the implant site. The site is prepared by peeling back gum tissue and drilling into the jaw bone. A fixture is then screwed or pressed into place in the jaw bone and the site is covered from about 3 to about 6 months to allow bone to grow around the implant and stabilize it in the jaw bone. After this period, the top of the fixture 50 is exposed and an abutment 52 is attached to the fixture. A crown 54, having a socket corresponding to the abutment, is then anchored to the abutment using an abutment screw 56 of the inventive alloy to complete the method of implantation. The fixture 50 is prepared from the inventive alloy. The abutment 52 and any screws 56 are also fabricated from the inventive alloy. The crown 54 is fabricated to include an abutment made from the inventive alloy, that is suitably coated to provide the appearance of a natural tooth.

FIG. 7A shows a defibrillator including a flexible silicone polymeric patch 60 with a coil of conductive wire 62 (typically titanium, stainless steel, or cobalt-nickel-chromium) on the side of the silicone patch 60 that will contact muscle tissue. When in place in the body, the lead wire 64 that carrier power to the coil 62 may extend out of the body (through the skin) and is electrically connected to a power source in a protective container 66. According to the invention, the lead wire 64 is fabricated with the invention titanium alloy. FIG. 7B is a cross-section of the lead wire 64. The power source 60, if implanted, can also be contained in a shell of the invention alloy.

Use of the Inventive Alloy in Non-Medical Applications

Many of the characteristics and physical properties which make the inventive alloy particularly suited in the manufacture or fabrication of structures, products and devices for medical applications also make the inventive alloy particularly suited in the manufacture or fabrication of a variety of structures, products and devices for non-medical applications. As described previously, the presence of Titanium and Hafnium in the alloy provides a non-medical structure, product or device that is well suited for use in corrosive environments. Further, the inclusion of molybdenum in the alloy, as described previously, provides a non-medical structure, product, or device that is highly resistant to corrosion in chloride, acidicy or basic environments and to stress-induced cracking.

An important characteristic of the inventive alloy is that the alloy may be further developed in a number of ways to obtain various combinations of properties. Thus, an alloy product intended for the fabrication of a certain structure, product or device may be further developed, through one or more methods, to obtain a unique combination of physical properties particularly desirable in that structure, product or device. For example, a near beta titanium alloy may be quenched to form a tough, ductile, strong martensitic microstructure and, in one method, this martensitic microstructure is aged to produce an alloy having increased strength and increased bulk hardness. In the alternative, the martensitic structure may be cold worked to obtain increased strength but also to dramatically reduce the elastic modulus (i.e., very low stiff-ness). Further, the martensitic microstructure may be hardened to obtain a hardness (above Rc 40) that exceeds the typical bulk hardness of present titanium alloys, and further yet to form a still harder conversion oxide or nitride ceramic-like surface layer. Through yet another method, an alloy product having very high strength (above 190 KSI) and hardness (about Rc 43) may be produced by heating the alloy above beta (835° C.) and then air cooling it. This enables a structure, product or device made substantially of the inventive alloy to be cold-worked to improve its strength and flexibility, but have locally heat-treated regions exhibiting high bulk hardness for reduced flexibility and improved friction and wear characteristics.

Exemplary uses of the inventive alloy in the manufacture or fabrication of additional structures, products and devices follow. Hereinafter, the term "article" or "article of manufacture" shall mean any structure, product or device, or, components or portions thereof, contemplated by the invention for medical or non-medical application of the inventive alloy. However, it should be understood that the present invention contemplates the use of the inventive alloy in the manufacture or fabrication of other articles (for medical and non-medical applications) which are not described or illustrated herein, but the the manufacture or fabrication of which will become apparent to one skilled in the art upon reading the Description and viewing the Drawings. Accordingly, the invention is not to be limited to the articles and methods described herein.

In one application, the inventive alloy is used as the primary construction material for a tubular shaft 72 of a golf club 70 (see FIG. 8). Preferably, the alloy for the tubular shaft 72 is cold worked to obtain high strength and high flexibility. Then, the tubular shaft 72 may be locally heat-treated, such as by aging or heating and air cooling, to obtain a desired stiffness of the shaft 72 without affecting its strength. In this manner, a tubular shaft 72 according to the invention may be custom designed to provide a shaft swing response particular to the user-golfer. Further adjustments to the shaft swing response may be made quickly (e.g., on site) by heat treating the tubular shaft 72.

The face 74 of the golf club iron 70 (or the head of a driver) may be made of the inventive alloy to provide a face (or head) having a low modulus (high flexibility), and which has additional elastic energy that is transferable to the golf ball. In this respect, such a face (or club head) is referred to as having a bigger "sweet spot." Alternatively, the face 74 of the club iron 70 may be aged to harden, thereby providing a surface having a higher resistance to wear and effecting a better, longer bite to the ball during ball-face impact or collision. In a further embodiment, the face may be conversion surface hardened to form a wear resistant, low friction ceramic surface layer, and thus produce a surface having reduced friction against the ball. This type of treatment to the face improves wear and scratching resistance, and the tendency of the club to slice the golf ball.

Figure 10:
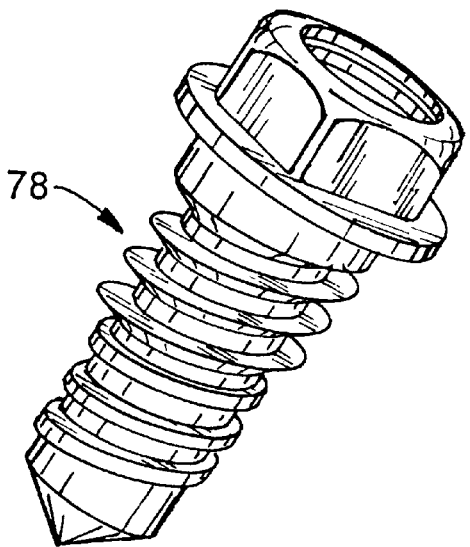
FIG. 10 is a perspective view of a second screw according to the invention.
Figure 9:
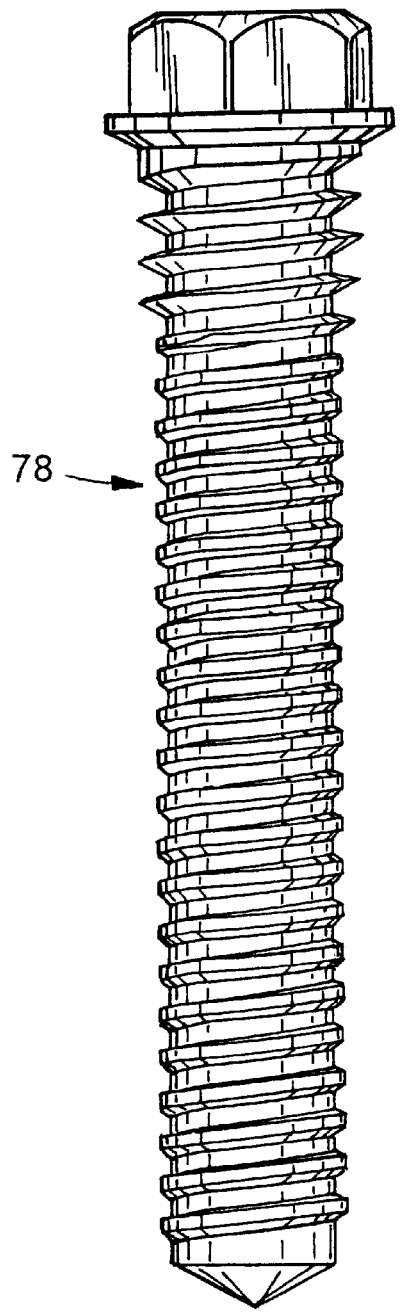
FIG. 9 is a side view of a screw according to the invention.

In another embodiment of the invention, a fastener, such as a rivet, bolt, or a screw 78, as depicted in FIGS. 9 and 10, is constructed of the inventive alloy. The screw according to the invention exhibits high strength but is deformable, and can be locally heat treated to alter its strength, hardness and stiffness, in accordance with the material to which it is to be fastened. In particular, a fastener according to the invention (e.g., a screw, bolt, etc.) is preferably cold worked to provide high strength and a lower modulus. The fastener will exhibit improved threading engagement due to the lower modulus and improved fastening torque properties due to its high strength. Such a fastener can function as a built-in lock washer. It should be noted that such properties can also be obtained for and prove useful in gears, suspensions, chains, valves, connector rods, turbines, and springs.

Figure 11:
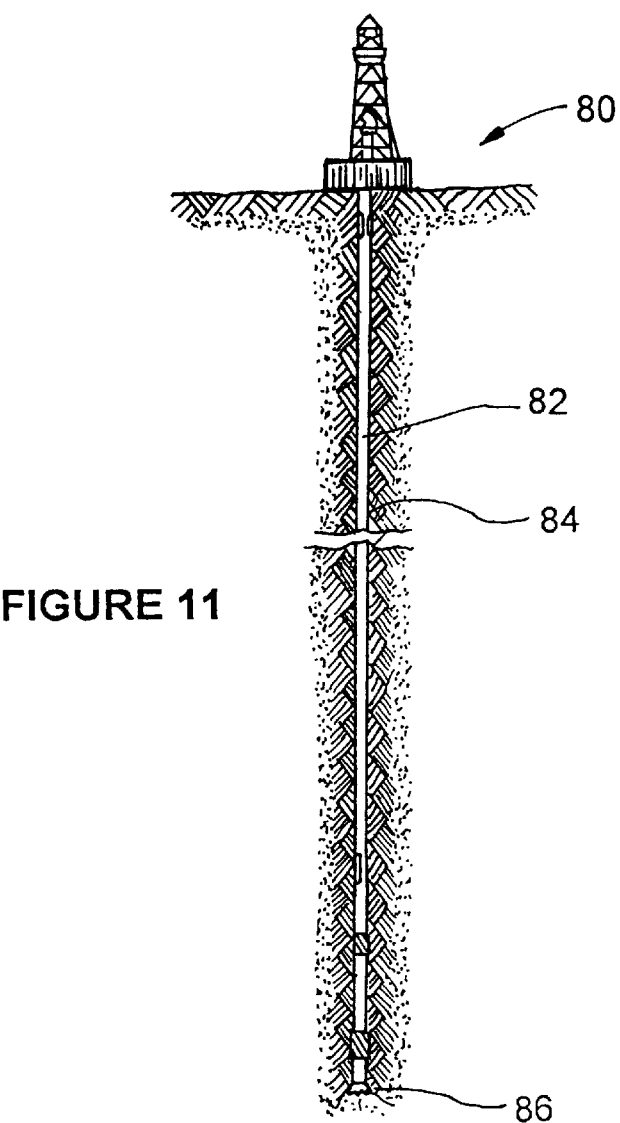
FIG. 11 is an elevation view of a drilling rig and drilling rig components according to the invention.

Articles may be made of the inventive alloy for service in oil/sour gas environments, such as equipment used in conjunction with a drilling rig 80 (as in FIG. 11). For example, the inventive alloy is suitable in the fabrication of components of a drill string 82 for drilling a well bore 84, drill sleeves and/or drill bits 86, because of its lightweight, high strength, high hardness and corrosion resistant properties. In one aspect of the invention, the inventive alloy may be formed with a bulk hardness above Rc 40 and/or a still harder conversion oxide or nitride surface layer. These properties make the inventive alloy a preferable material for many types of heavy, stiff, lower strength liners, drill shafts and bits. Due to its lightweight and high strength properties, the inventive alloy is particularly suited for the fabrication of shafts to be directed for miles underground or to the ocean floor.

Figure 12:
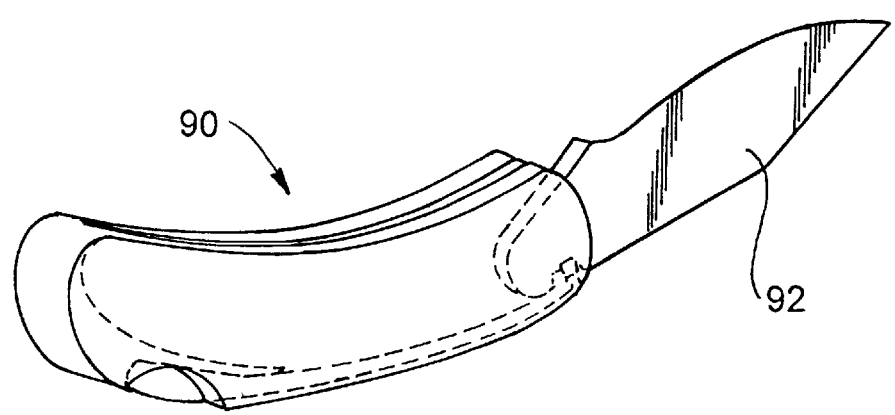
FIG. 12 is a perspective view of a cutting knife according to the invention.

Further, the combination of light weight, high strength and high hardness properties (and associated wear resistant properties) attainable in the inventive alloy are particularly suitable and advantageous in drill bits, grinders, and cutting instruments such as knives and other cutlery. For example, the knife 90 depicted in FIG. 12 is equipped with a blade component 92 made of the inventive alloy.

The inventive alloy also proves advantageous in the fabrication of seals and valves. Seals and shafts made of the inventive alloy may be fabricated with high hardness and low friction properties, and also with varying strength and toughness. Because the inventive alloy is unique in developing a bulk hardness above Rc 40, such seals and shaft may be finely polished to degrees of tolerance and precision which are not attainable with typical soft titanium alloys. The alloy surfaces of the seal or valve of the invention may also be conversion surface oxidized after being polished into a hardened condition, thereby producing an even harder, low friction surface. Seals and valves according to the invention also exhibit improved wear resistant and corrosion resistant properties.

The inventive alloy is also suitable for use in custom plating or fabrication of electrical components which require insulative and/or wear resistant regions. A plate component made or formed with the inventive alloy is preferably cold worked to obtain high strength and flexibility. The regions around holes and/or apertures formed in the plate may be locally heat treated to increase its hardness, wear resistance (more fretting resistant), and stiffness. In this way, the holes and apertures will have a reduced effect on the overall rigidity of the plate and the regions around the holes do not have to be built up to compensate for the reduced rigidity.

The above-described articles are just some of the articles which may be advantageously fabricated with or from the inventive alloy. The inventive alloy is also particularly suited for use as a construction material for shock-absorbing suspensions and landing gears, where high strength and flexibility are desirable for "built-in" shock absorption. Other articles which may be advantageously fabricated from or with the inventive alloy include connecting rods, piston rings, gears, turbine compressing blades, chemical storage and pressure vessels, knives and cutting instruments, armor, saltwater propellers, and marine and fishing gear. It should be understood, however, that, upon reading the Description and viewing the Drawings provided herein, it will be apparent to one skilled in the art to adapt the present inventive alloy in a variety of applications, wherein the advantageous properties obtainable with the inventive alloy may be beneficial.

Although the present invention has been described with reference to its preferred embodiments, those skilled in the arts will recognize changes that may be made in form and structure which do not depart from the spirit of the invention already described in the specification and embodied in the claims which follow.

What is claimed is:

1. A titanium alloy comprising:
   a) titanium;
   b) between about 5 and about 11 weight percent molybdenum;
   c) between about 6 and about 15 weight percent hafnium; wherein the alloy provides for high-strength and hardness, low elastic modulus, enhanced corrosion resistance, and surface hardening.

2. The titanium alloy of claim 1, further comprising niobium partially substituting for a weight percentage of molybdenum.

3. The titanium alloy of claim 1, wherein the alloy further includes up to about 2 to about 3 weight percent of at least one element selected from the group consisting of iron, chromium and silicon.

4. The titanium alloy of claim 1, wherein the alloy includes, about 5 to 9 weight percent molybdenum, and about 6 to 9 weight percent hafnium.

5. The titanium alloy of claim 1, wherein the alloy comprises about 7 weight percent molybdenum and about 7 weight percent hafnium.

6. The titanium alloy of claim 1, wherein the alloy further includes trace levels of at least one element selected from the group consisting of oxygen, nitrogen, hydrogen and carbon.

7. An article of manufacture having at least one portion partially fabricated from a metal alloy comprising:
   a) titanium;
   b) between about 5 and about 11 weight percent molybdenum;
   c) between about 6 and about 15 weight percent hafnium; wherein the alloy provides for high-strength and hardness, low elastic modulus, enhanced corrosion resistance, and surface hardening of said portion of said article.

8. The article of claim 7, wherein the alloy further includes up to about 2 to 3 weight percent of at least one element selected from the group consisting of iron, chromium and silicon.

9. The article of claim 7, wherein additional interstitial strengthening of the alloy is achieved by increased levels of an element selected from the group consisting of oxygen, nitrogen, hydrogen and carbon.

10. The article of claim 7, wherein the alloy composition is titanium, about 5 to 9 weight percent molybdenum, and about 6 to about 9 weight percent hafnium.

11. The article of claim 7, wherein the alloy composition is titanium, about 7 weight percent molybdenum and about 7 weight percent hafnium.

12. The article of claim 7, wherein said portion of said article is surface hardened by a process selected from the group consisting of oxidation and nitriding to form a hard, diffusion bonded, conversion surface oxide or nitride.

13. The article of claim 12, wherein said portion of said article is coated with a low friction coating.

14. The article of claim 7, wherein the alloy is mechanically hot-worked to optimize the grain size, strength, modulus, and toughness of the alloy.

15. The article of claim 7, wherein the alloy is cold worked to optimize the grain size, strength, modulus, and toughness of the alloy.

16. The article of claim 15, wherein the alloy is an alloy that is at least partially heat treated after being cold-worked.

17. The article of claim 15, wherein the alloy is an alloy that is at least partially heat treated by an aging treatment after being cold-worked.

18. The article of claim 15, wherein the alloy is an alloy that is heat treated above about 900° C. and then air cooled.

19. The article of claim 7, wherein the alloy is a near beta titanium alloy that is quenched to form a martensitic microstructure and then aged to increase strength and bulk hardness.

20. The article of claim 7, wherein the alloy is a near beta titanium alloy that is quenched to form a martensitic microstructure and then cold-worked to increase alloy strength and reduce alloy elastic modulus.

21. A titanium alloy suitable for use in the fabrication of a variety of articles, said alloy comprising:
   (a) titanium;
   (b) between about 5 to about 11 weight percent molybdenum;
   (c) between about 6 to about 15 weight percent hafnium;
   (d) up to about 2 to about 3 weight percent of at least one element selected from the group consisting of iron, chromium and silicon;
   (e) trace levels of an element selected from the group consisting of oxygen, nitrogen, hydrogen, and carbon; and
      wherein the alloy provides for high-strength and hardness, low elastic modulus, enhanced corrosion resistance, and surface hardening.

22. The titanium alloy of claim 21, further comprising between about 5 to about 10 weight percent niobium.

23. The titanium alloy of claim 21, further comprising niobium partially substituting for a weight percentage of molybdenum.

* * * * *